United States Patent [19]

Chu et al.

[11] Patent Number: 4,481,364
[45] Date of Patent: Nov. 6, 1984

[54] PREPARATION OF AMINOPROPYLTRIALKOXYSILANES AND/OR AMINOALKYLALKOXYSILANES

[75] Inventors: Nan S. Chu, Hartsdale; Bernard Kanner, West Nyack; Curtis L. Schilling, Jr., Croton-on-Hudson, all of N.Y.

[73] Assignee: Union Carbide Corporation, Danbury, Conn.

[21] Appl. No.: 535,615

[22] Filed: Sep. 26, 1983

[51] Int. Cl.$^3$ ............................ C07F 7/08; C07F 7/10; C07F 7/18
[52] U.S. Cl. ........................................................ 556/413
[58] Field of Search .................................................. 556/413

[56] References Cited

U.S. PATENT DOCUMENTS

| | | | |
|---|---|---|---|
| 2,721,873 | 10/1955 | MacKenzie et al. | 556/413 X |
| 2,762,823 | 9/1956 | Speier et al. | 556/413 |
| 3,470,225 | 9/1969 | Knorre et al. | 556/413 |
| 3,665,027 | 5/1972 | Reichel | 556/413 |
| 3,864,373 | 2/1975 | Sebler et al. | 556/413 |

FOREIGN PATENT DOCUMENTS

| | | | |
|---|---|---|---|
| 165746 | of 1975 | Czechoslovakia | 556/413 UX |
| 193448 | of 1979 | Czechoslovakia | 556/413 UX |
| 151944 | of 1980 | German Democratic Rep. | 556/413 UX |
| 372228 | 7/1973 | U.S.S.R. | 556/413 UX |
| 415268 | 7/1974 | U.S.S.R. | 556/413 UX |
| 505647 | 3/1976 | U.S.S.R. | 556/413 UX |
| 534459 | 2/1977 | U.S.S.R. | 556/413 UX |
| 724515 | 3/1980 | U.S.S.R. | 556/413 UX |

OTHER PUBLICATIONS

Zh. Obsach Khim. 42, 858–862, (1972).
Chem. Abstracts 93:150371f.

Primary Examiner—Paul F. Shaver
Attorney, Agent, or Firm—Paul W. Leuzzi, II

[57] ABSTRACT

A platinum catalyzed addition of allylamine and N-substituted allyl amines to trialkoxysilanes or alkylalkoxysilanes is improved by running the reaction under pressure at 110°–210° C. and in the presence of a reaction promoter. As a result, the time and the amount of platinum catalyst required for the reaction are significantly reduced and conversion and yield of the product increased.

26 Claims, No Drawings

PREPARATION OF AMINOPROPYLTRIALKOXYSILANES AND/OR AMINOALKYLALKOXYSILANES

BACKGROUND OF THE INVENTION

1. Field of the Invention

The instant invention relates to a novel process for preparing aminopropyltrialkoxysilanes and/or aminoalkylalkoxysilanes. More specifically, the invention relates to the platinum catalyzed addition of allylamine or N-substituted allylamines with trialkoxysilanes or alkylalkoxysilanes under pressure at 110° to 210° C. in the presence of a reaction promoter.

2. The Prior Art

The platinum catalyzed addition of allyl amine or N-substituted allylamines to trialkoxysilanes (I) offers a direct route to aminopropyltrialkoxysilanes. This reaction is well

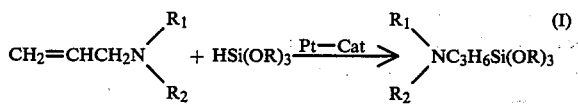

known and has been studied by many investigators. However, in order to obtain a reasonable conversion and yield, the process requires long reaction time and-/or high platinum catalyst concentrations. For instance, U.S. Pat. No. 3,665,017 teaches the preparation of γ-aminopropyltriethoxysilane and γ-aminopropylalkylalkoxysilanes by refluxing allyl amine with hydrogenalkoxysilanes or hydrogenalkylalkoxysilanes in the presence of a platinum catalyst until the temperature of the reaction mixture reaches a constant level above 110° C. The time required to reach the final temperature varied from 10 to 60 hours, depending upon the platinum catalyst concentration used and the presence or absence of a solvent having a higher boiling point than the components that were to be added to one another. Therefore, when a mixture of allyl amine and triethoxysilane containing 5% of ethyl silicate was heated in the presence of approximately 200 ppm platinum (as $H_2PtCl_6$), the temperature of the reaction rose to 190° C. in 14 hours to give a 71–79% yield of the desired product. But the time required increased to more than two days (56 hours) when the platinum catalyst concentration was decreased to about 66 ppm. Similarly, in U.S. Pat. No. 3,864,373 mixtures of γ- and β-aminopropyltriethoxysilane were prepared by heating allyl amine with trialkoxysilane in the presence of a platinum catalyst such as mesityl oxide platinum dichloride until the sump temperature reached approximately 135° C. or for 24 hours (Zh., Obshch Khim, 42, (4), 858–862 (1972)). In the latter case, the temperature of the reaction mixture rose from 74° C. to 125° C. during the 24 hour heating period and the yield of aminopropyltriethoxysilane was in the range of 60 to 67%. Two Czech Patents obtained 57–71% of γ-aminopropyltriethoxysilane by heating the reactants from 70°–150° C. in the presence of $(CH_2=CHCH_2NH_3)^+PtCl_3^-$ (Czech C S No. 165,746) or of $(Ph_3P)_4Pt$ or $(Ph_3P)_2PtX_2$ (193.448).

Recently, a continuous process for the preparation of aminoalkoxysilanes was disclosed (Ger. (East) No. DDR151944). Thus the addition of organohydrosilanes to allyl amine in the presence of a solution or suspension of an addition catalyst in multi-stage, heatable reaction apparatus was carried out under ambient pressure in the temperature range of 110°–135° C. and with a contact time of from 3600–2400 seconds. According to the process, the reaction time was shortened considerably. However, the process requires several reactors and high platinum concentration (>200 ppm).

Aminopropyltriethoxysilanes have also been prepared by heating the reactants in the presence of a platinum catalyst and a promotor (or co-catalyst) such as unsaturated ether (USSR No 372,228), ketone, carboxylic acids, keto-acids and esters (USSR No. 415,268) allyl alcohol (USSR No. 505647), epichlorohydrin (USSR No. 724,459) and dicarbon-nidoundecaborate $K(C_2B_9H_{12-n}R_n^-K^+)$ (USSR No. 724,515). These reactions generally were carried out at atmospheric pressure and the platinum catalyst and promoter were heated together with allyl amine and the corresponding trialkoxysilane until the temperature of the reaction mixture reached 120° C. or higher. For example, aminopropyltrialkoxysilanes were prepared by treating trialkoxysilanes with allyl amine in the presence of $H_2PtCl_6$ (100 ppm) and 0.1–1.5% epichlorohydrin for 9–11 hours until the temperature of the mixture reached 120° C. and then held at that temperature for another 2–3 hours. Yield of the aminosilanes was in the range of 58–70%. V. Vybrial and his coworkers have also studied the effect of various promoters which included: triphenylphosphine, triphenylarsine, carboxylic acids and their esters and some carbonyl compounds. The best modifier found was triphenylphosphine. When used in conjunction with $H_2PtCl_6$ (~350 ppm Pt), it shortened the reaction time from 9.7 hours ($H_2PtCl_6$ alone) to 6.5–7.3 hours. All these results indicate that even with 100–200 ppm of Pt, extensive reaction time is required in order to obtain reasonable conversions and yields.

OBJECT OF THE INVENTION

It is a primary object of the invention to provide a process for preparing aminotrialkoxysilanes and aminoalkylalkoxysilanes with a significantly reduced amount of platinum catalyst.

Another object of the invention is to obtain increased yields of aminotrialkoxysilanes and aminoalkylalkoxysilanes.

A third object of the invention is to shorten the reaction time necessary to provide acceptable yields of aminotrialkoxysilanes and aminoalkylalkoxysilanes.

Other objects of the invention will be made apparent from the detailed description and examples set forth herein.

SUMMARY OF THE INVENTION

The present invention provides an improved process for preparing beta- and gamma- aminotrialkoxysilanes and aminoalkylalkoxysilanes. It has been found that by running the addition reaction between allylamine and-/or N-substituted allylamine with trialkoxy-silanes and-/or alkylalkoxysilanes under pressure, at high initial temperatures, in the presence of a reaction promoter, the efficiency of the platinum catalyst is greatly increased. As a result of this improved process, the platinum catalyst concentration necessary to obtain an acceptable yield can be greatly reduced, while at the same time significantly shortening the reaction time. Furthermore, the yield of aminopropyltrialkoxy-silanes and/or aminoalkylalkoxysilanes obtained is improved, as is the conversion percentage. The high conversion and yields achieved by such reduced amounts of platinum catalyst have previously never been observed. Indeed, U.S. Pat. No. 3,665,027 stated that reduced yields and conversion of aminopropyltrialkoxysilanes would be expected when the addition reaction is carried out under pressure and at higher temperatures than reflux.

DETAILED DESCRIPTION OF THE INVENTION

In accordance with the present invention there is provided a novel process for preparing aminopropyltrialkoxysilanes and aminoalkylalkoxysilanes. The reaction is generally represented by the sequence:

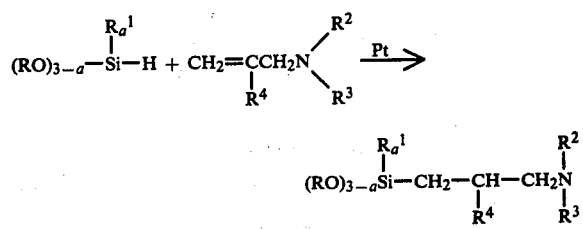

Suitable silanes are those selected from the group represented by the general formula:

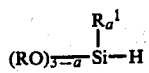

wherein a is zero, one or two, and R and $R^1$ are individually monovalent hydrocarbon radicals containing from one to ten carbon atoms, inclusive. Preferably, a is zero or one and R and $R^1$ are methyl or ethyl groups. Illustrative of suitable silanes are triethoxysilane, trimethoxysilane, tripropoxysilane, tri-isopropoxysilane, tributoxysilane, methyldi-methoxysilane, ethyldimethoxysilane, methyldiethoxy-silane, dimethylmethoxysilane, trioctyloxysilane, methyldioctyloxysilane, dimethyloctyloxysilane, and the like.

Suitable amines useful in the present invention are those selected from the group represented by the formula:

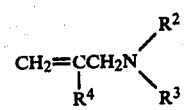

wherein $R^2$ and $R^3$ are independently selected from the group consisting of hydrogen, monovalent hydrocarbon groups containing from one to ten carbon atoms inclusive, phenyl or substituted phenyl groups

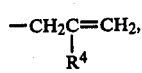

and $+CH_2CH_2NH)_nH$ wherein n is 1 to 4 and $R^4$ is individually either hydrogen or a methyl group. Preferably the amine is alkylamine where $R^2$ and $R^3$ are both hydrogen. Illustrative of suitable amines are allylamine, N,N-dimethylallylamine, N,N-diethylallylamine, N-allylaniline, methallylamine, diallylamine, triallylamine, and the like.

The ratio of silane to amine can be varied from 1.5:1 to 1:1.5, and preferably is within the range of 1.1:1 to 1:1.1 when allylamine and its derivatives are employed.

The ratio of silane to amine will change to 2.0:1 to 2.5:1 when diallylamine and its derivatives are employed and 3.0:1 to 4.5:1 when triallylamine and its derivatives are used.

The reaction temperature and resultant pressure play an important role in the improved process. Suitable reaction temperatures range from 110° to 210° C. and preferably in the range of from 130° to 170° C. The pressure will be a function of the boiling point of the reactants. Generally, the reaction will take place in a closed system to avoid volatilization of one or more of the reactants when its boiling point is below the operating temperatures, this in turn will result in increased operating pressures as the system approaches its operating temperature.

The reaction time will depend upon other conditions, such as the amount of platinum catalyst or the temperature of reaction. As would be expected, the higher the catalyst concentration and reaction temperature, the shorter the reaction time. Generally, when the platinum catalyst concentration is in the range of 10-20 parts per million, the reaction temperature is within the range of 130° to 170° C. A reaction time on the order of two to five hours is sufficient to obtain acceptable yields. Longer reaction times will not significantly increase the yield, but they may be desirable in certain instances. The platinum-containing hydrosilation catalyst may be chosen from the group of supported platinum catalysts such as platinum on γ-alumina or on charcoal, or from the group of soluble platinum complexes, such as chloroplatinic acid, bis(ethylene platinous) chloride, cis-dichlorodiamine platinum (II), platinum (II) acetylacetonate, platinum (O) or other soluble platinum complexes well known in the art. The soluble platinum complexes are normally used as solutions in solvents such as isopropanol or 1,2-dimethoxyethane. The concentration of the platinum-catalyst required depends on reaction temperature and time but is generally used in the range of 5-30 ppm and preferably 10-25 ppm based on the total weight of the silane and amine used. Higher catalyst concentrations are not necessary nor economical.

The use of a reaction promoter is preferable but not absolutely necessary. However, the presence of a reaction promoter is needed to further accelerate the rate of the reaction and increase the conversion of the reaction. The reaction promoter should be employed at a concentration of 0.5 to 10 mole percent of the silane charge, and preferably 1.5 to 2.5 mole percent of the silane charged. Suitable reaction promoters include, but are not limited to, the alkali-metal carbonates or bi-carbonates, such as potassium carbonate, potassium bicarbonate, sodium carbonate, sodium bicarbonate, cesium carbonate, cesium bicarbonate, rubidium carbonate, rubidium bicarbonate, lithium carbonate, lithium bicarbonate, barium carbonate, barium bicarbonate, strontium carbonate, strontium bicarbonate, calcium carbonate, calcium bicarbonate, and the like.

The resulting aminopropyltrialkoxysilane and aminoalkylalkoxysilane obtained are mixtures of beta- and gamma-isomers and are generally represented by the formulae:

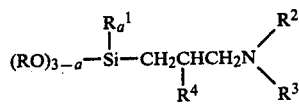

-continued
gamma-isomer

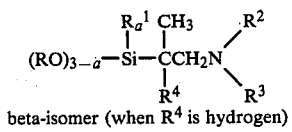

beta-isomer (when $R^4$ is hydrogen)

wherein R, $R^1$, $R^2$, $R^3$, $R^4$ and a are as previously defined. The resulting amino propyltrialkoxysilane and aminoalkylalkoxysilane are generally recovered in high yields and conversions when the catalyst concentration and temperature of the invention are employed as is demonstrated in the examples.

Illustrative of such products include the beta- and gamma-isomers of aminopropyltrimethoxysilane, aminopropyltriethoxysilane, aminopropylmethyldimethoxysilane, aminopropyltri-isopropoxysilane, N-phenylaminopropyltriethoxysilane, N-phenylaminopropylmethyldiethoxysilane, tris-(triethoxysilylpropyl)amine, bis-(triethoxysilylpropyl)amine, tris-(trimethoxysilylpropyl)amine, bis-(trimethoxysilylpropyl)amine, N-(beta-aminoethyl)aminopropyltriethoxysilane, and the like.

Aminopropyltrialkoxysilanes and aminoalkylalkoxysilanes find general utility as potential glass-plastic coupling agents, bonding aids, additives to phenolic binder/foundry mixtures, adhesion promoters for vinyl plastisols, polyurethane elastomers, and epoxy and acrylic-based inks.

Whereas the exact scope of the instant invention is set forth in the appended claims, the following specific examples illustrate certain aspects of the present invention and, more particularly, point out methods of evaluating the same. However, the examples are set forth for illustration only and are not to be construed as limitations on the present invention except as set forth in the appended claims. All parts and percentages are by weight unless otherwise specified.

EXAMPLE 1

Into a $N_2$ purged 45 ml Parr bomb equipped with a pressure gauge, were added 0.07 grams of anhydrous $Na_2CO_3$, 9.2 ml of triethoxysilane, 3.8 ml of allyl amine and 15 ppm of Pt (as $H_2PtCl_6$) under $N_2$. The bomb was placed in a fluidized sand bath which was pre-heated to 130° C. and left there for 6.5 hours. At the end of the reaction, the bomb was taken out and cooled with ice-water. The content of the reaction mixture was analyzed with a Hewlett-Packard 5830-A gas chromatograph (G.C.).

The gas chromatograph was equipped with a 10 ft. column packed with 10% UC-W98 on Chromasorb 750 (80/100 mesh). The GC conditions used were: He 29–32 ml/min., Inj. Port 300° C., detector 350° C., program 90° C. for four min. then 90°–250° C. at a rate of 20°/min.

The conversion and yield of aminopropyltriethoxysilane were determined according to the internal standard method well known in the art. It was found that the conversion and yield of the reaction based on the triethoxysilane used were 71.3% and 86.6% respectively. The ratio of gamma to beta isomers was 3.9:1.

EXAMPLE 2

The same procedure of Example 1 was used except that 0.1 gram of $Na_2CO_3$ was used and that the reaction temperature used was 140° C. Conversion and yield of the reaction were 79.1% and 81.4% respectively. The ratio of gamma to beta isomers was 4.7:1.

EXAMPLE 3

The sample procedure of Example 1 was used except that $Na_2CO_3$, 0.10 gram, was used and that the reaction was carried out at 130° C. for 12 hours. Conversion and yield of aminopropyltriethoxysilane were 80.5% and 83.4% respectively. The ratio of gamma to beta isomers was 4.2:1.

EXAMPLE 4

The same procedure of Example 3 was used except that no anhydrous $Na_2CO_3$ was used. Percent conversion and yield of the reaction were 60.5% and 85.6% respectively. The ratio of gamma to beta isomers was 4.4:1.

EXAMPLE 5

In order to find the actual time required under the conditions used, Swagelok capped stainless steel tubes (3 ml capacity) were used as reactors. For each run, a batch of reaction mixture (i.e., 9.2 ml $(EtO)_3SiH$, 3.8 ml allyl amine and 15 ppm of Pt (as $H_2PtCl_6$)) was made and transferred (each 1.2 ml) to the tubes which contained the desired amount of anhydrous $Na_2CO_3$ (0.0092 g). The small reactors were placed in a rocker and heated with a fluidized sand bath preheated to 130° C. At desired time intervals, the tubes were taken out, cooled with ice-water and analyzed. The formation of aminopropyltriethoxysilane was completed within 3.5 hours.

EXAMPLE 6

The same procedure of Example 5 was used except that no $Na_2CO_3$ was used. The results obtained demonstrates again that the hydrosilation took place quite well at 15 ppm of Pt level even without $Na_2CO_3$ but after 3.5 hours the reaction was only 82.5% as complete as that of Example 5, and even after 6 hours the results of Example 5 were not obtained.

EXAMPLE 7

The same procedure of Example 5 was used except that the temperature used was 150° C. The time required for this reaction to achieve the results of Example 5 was about 2 hours.

EXAMPLE 8

The same procedure of Example 5 was used except that 10 ppm of Pt (as Pt (II) acetyl acetonate) was used. The hydrosilation went well even with such low amount of Pt-level, achieving results similar to those reported in Example 6 in 1.6 hours.

EXAMPLE 9

Into a 50 ml 3-necked round bottom flask, fitted with a condenser, a thermometer, and $N_2$ inlet tubing, were added 9.6 ml of triethoxysilane, 4.2 ml of allyl amine and 100 ppm of Pt (as $H_2PtCl_6$). The reaction mixture was heated at refluxing temperature for 24 hours until the temperature of the reaction mixture reach 108° C. GC analysis of the reaction mixture showed that percent conversion and yield of the reaction were 33.6 and 67.4% respectively. The gamma to beta isomer ratio was 8.3:1.

Comparison of the result obtained from this experiment with those obtained from examples 1–8 indicates clearly the effect of temperature.

EXAMPLE 10

The same procedure of Example 9 was used except that 0.22 gm of anhydrous $Na_2CO_3$ was used together with the 100 ppm of Pt. The temperature of the reaction reached 101° C. in 4.5 hours. Percent conversion and yield of aminopropyltriethoxysilane were 55.4 and 71.2% respectively. The gamma to beta isomer ratio was 14.6:1.

EXAMPLE 11

The same procedure of Example 9 was used except that 50 ppm of Pt (as $H_2PtCl_6$) was used instead of 100 ppm of Pt, and that 1.0 grams of $Na_2CO_3$ was used. The reaction temperature reached 100° C. after 7.3 hours. Percent conversion and yield of reaction were 41.2 and 67.5% respectively. The gamma to beta isomer ratio was 15.9:1.

The results from these examples indicate that addition of $Na_2CO_3$ as a promoter shortens the reaction time and improves the conversion of the reaction.

EXAMPLE 12

The procedure given in Example 3 was followed except that methyldiethoxysilane (9.6 ml) was used instead of triethoxysilane and that 4.5 ml of allyl amine was used. Percent conversion and yield of the reaction were 71.5 and 85.7% respectively. The gamma to beta isomer ratio was 8.0:1.

EXAMPLE 13

The same procedure given in Example 1 was followed except that the reactants used were: 0.20 gram of anhydrous $Na_2CO_3$, 9.6 ml of tri-isopropoxysilane, 3.8 ml of allyl amine and 20 ppm of Pt (as $H_2PtCl_6$). The reaction was heated at 140° C. to give a mixture of beta and gamma aminopropyltriisopropoxysilane isomers. Conversion and yield of reaction were 56.3% and 79.6% respectively.

EXAMPLE 14

The procedure of Example 1 was followed except that the reactants were: $Na_2CO_3$ 0.15 gram, triethoxysilane 9.2 ml, N-allylaniline 6.8 ml and 11.4 ppm of Pt (as $H_2PtCl_6$). The reaction mixture was heated at 130° C. for 7 hours.

The reaction product was analyzed with a 10 ft. column packed with 10% OV-101 on chromasorb W-HP. Program used was: 100° C. for one minute, 100°–325° C. at 15°/min. The major component of the reaction product was found to be a mixture of beta and gamma isomers of N-phenylaminopropyltriethoxysilane, which had 78.15% area % of the gas chromatogram.

EXAMPLE 15

The same Swagelok capped stainless tubes of Example 5 were used. A batch reaction mixture was made by mixing 9.2 ml of triethoxysilane with 3.8 ml of allyl amine. The mixture, 2.6 ml each, was then charged to the stainless tubes, each containing 0.0199 grams of anhydrous $Na_2CO_3$ and a desired amount of one of the Pt-catalysts listed in Table 1. The tubes were heated at 130° C. in a fluidized sand bath for 5 hours. Results obtained are summarized in Table 1.

TABLE 1
HYDROSILATION OF ALLYL AMINE WITH TRIETHOXYSILANE

| No. | Pt—catalyst | Wt of Pt—cat. (g) | Conv. % | Yield % | gamma/beta isomer ratio |
|---|---|---|---|---|---|
| 1 | $PtCl_2(Ph_3P)_2$ | 0.0002 | 66.7 | 76.1 | 5.9 |
| 2 | cis-$Pt(NH_3)_2Cl_2$ | 0.001 | 70.7 | 79.3 | 5.1 |
| 3 | $(Ph_3P)_4Pt$ | 0.004 | 66.2 | 74.7 | 5.9 |

EXAMPLE 16

The same procedure of Example 1 was used except that 0.1 gram of anhydrous $Na_2CO_3$ and 17 ppm of Pt were used and that the reaction was carried out at 200° C. for 5 hours. Conversion and yield of the reaction were 56.2 and 58.7% respectively. The gamma to beta isomer ratio was 3.2:1.

COMPARATIVE EXAMPLE A

The same procedure of Example 16 was used except that the reaction was carried out at 230° C. for 5 hours. Conversion and yield of the reaction were 41.6 and 41.9% respectively. Therefore although the reaction will take place at reaction temperatures higher than 210° C., yield and conversion of the desired product will drop because of other by-products formation. The gamma to beta isomer ratio was 2.8:1.

COMPARATIVE EXAMPLE B

The same procedure of Example 1 was used except that 0.44 gram of $Na_2CO_3$ and 66 ppm of Pt were used and that the reaction was carried out at 105°–106° C. for 5 hours. Yield and conversion of the reaction were 75.2 and 71.8% respectively. This result indicates that a higher amount of Pt-Catalyst is required when the reaction is carried out at reaction temperature lower than 110° C.

EXAMPLE 17

Into a 50 ml 3-necked round bottom flask, fitted with a condenser, a thermometer, an addition funnel and $N_2$ inlet-outlet tubing were added 0.44 g of anhydrous $Na_2CO_3$, 3.0 ml of diallylamine and 3.0 ml of triethoxysilane. The mixture was heated with an oil-bath at 120°–125° C. Platinum catalyst (15 ppm as $H_2PtCl_6$) was then added. Triethoxysilane was dropped in at such a rate that the temperature of the reaction mixture was maintained at 124°–126° C. After the addition of (EtO)$_3$SiH was completed, the mixture was heated at ~120° C. for 1.5 hours. Gas chromatographic analysis of the mixture indicated that the reaction gave a mixture of gamma- and beta-isomers of $((EtO)_3SiC_3H_6)_2NH$. The total GC area % of the isomers was 85.04%.

We claim:

1. An improved process for preparing aminoalkylalkoxysilanes which comprises reacting a hydrosilane of the general formula

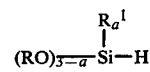

wherein a is zero, one or two, and R and R′ are individually monovalent hydrocarbon radicals containing from one to ten carbon atoms inclusive: with an amine of the general formula

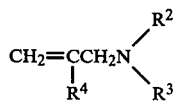

wherein $R^2$ and $R^3$ are individually selected from the group consisting of hydrogen, monovalent hydrocarbon radicals containing from one to ten carbon atoms inclusive, a phenyl or substituted phenyl group

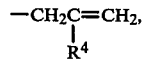

and $-(CH_2CH_2NH)_nH$, wherein n is 1 to 4 and $R^4$ is individually either hydrogen or a methyl group, said reaction taking place under pressure at a temperature of from 110° to 210° C. in the presence of a platinum-catalyst and, optionally, in the presence of a reaction promoter.

2. The process of claim 1 wherein the reaction temperature is from 130° C. to 170° C.

3. The process of claim 1 wherein the platinum catalyst concentration is from 5 to 30 ppm based on the total weight of the silane and amine charge.

4. The process of claim 3 wherein the platinum catalyst concentration is from 10 to 25 ppm based on the total weight of the silane and amine charge.

5. The process of claim 1 wherein the reaction promoter is used at a concentration of 0.5 to 10 mole percent of the silane charge.

6. The process of claim 5 wherein the reaction promoter is used at a concentration of from 1.5 to 2.5 mole percent of the silane charge.

7. The process of claim 1 wherein the silane is such that a is zero or one and R and $R^1$ are either methyl or ethyl groups.

8. The process of claim 1 wherein the amine is such that $R^2$, $R^3$ and $R^4$ are all hydrogen.

9. The process of claim 1 wherein the amine is methallylamine.

10. The process of claim 1 wherein the amine is diallylamine.

11. The process of claim 1 wherein the amine is triallylamine.

12. The process of claim 1 wherein the ratio of silane to amine as such is between 1.5:1 to 1:1.5 when the amine is alkylamine or its derivative, 2.0:1 to 2.5:1 when the amine is diallylamine or its derivative, and 3.0:1 to 4.5:1 when the amine is triallylamine or its derivative.

13. The process of claim 1 wherein the reaction promoter is an alkali-metal carbonate or bicarbonate.

14. An improved process for preparing aminoalkylalkoxysilanes which comprises reacting a hydrosilane of the general formula:

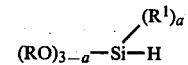

wherein a is zero or one, and R and $R^1$ are individually ethyl or methyl groups with an amine of the general formula

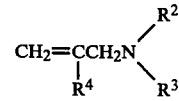

wherein $R^2$, $R^3$ and $R^4$ are as defined in claim 1, said reaction taking place under pressure at a temperature of from 130° to 170° C. in the presence of a platinum catalyst and a reaction promoter.

15. The process of claim 14 wherein the platinum catalyst concentration is from 5 to 30 ppm based on the total weight of the silane and amine charge.

16. The process of claim 14 wherein the platinum catalyst concentration is from 10 to 25 ppm based on the total weight of the silane and amine charge.

17. The process of claim 14 wherein the reaction promoter is used at a concentration of 0.5 to 10 mole percent of the silane charge.

18. The process of claim 14 wherein the reaction promoter is used at a concentration of from 1.5 to 2.5 mole percent of the silane charge.

19. The process of claim 14 wherein the amine is such that $R^2$, $R^3$ and $R^4$ use all hydrogen.

20. The process of claim 14 wherein the amine is methallylamine.

21. The process of claim 14 wherein the amine is diallylamine.

22. The process of claim 14 wherein the amine is triallylamine.

23. The process of claim 14 wherein the ratio of silane to amine as such is between 1.5:1 to 1:1.5 when the amine is allkylamine or its derivative, 2.0:1 to 2.5:1 when the amine is diallylamine or its derivative, and 3.0:1 to 4.5:1 when the amine is triallylamine or its derivative.

24. The process of claim 14 wherein the reaction promoter is an alkali-metal carbonate or bicarbonate.

25. The process of claim 24 wherein the reaction promoter is sodium carbonate.

26. The process of claim 24 wherein the reaction promoter is sodium bicarbonate.

* * * * *